United States Patent [19]

Serajuddin et al.

[11] Patent Number: 5,433,951
[45] Date of Patent: Jul. 18, 1995

[54] SUSTAINED RELEASE FORMULATION CONTAINING CAPTOPRIL AND METHOD

[75] Inventors: Abu T. M. Serajuddin, Flushing, N.Y.; Michael G. Fakes, East Windsor, N.J.

[73] Assignee: Bristol-Myers Squibb Company, Princeton, N.J.

[21] Appl. No.: 136,436

[22] Filed: Oct. 13, 1993

[51] Int. Cl.$^6$ .............................. A61K 9/22
[52] U.S. Cl. .................... 424/486; 424/468; 424/502
[58] Field of Search ............... 424/486, 501, 502, 497, 424/468, 502

[56] References Cited

U.S. PATENT DOCUMENTS

| | | | |
|---|---|---|---|
| 4,464,363 | 8/1984 | Higuchi et al. | 424/232 |
| 4,797,286 | 7/1989 | Thakkar et al. | 424/456 |
| 5,028,432 | 7/1991 | Chopra et al. | |
| 5,169,645 | 12/1992 | Shukla et al. | 424/499 |

OTHER PUBLICATIONS

C. Doelker et al, "The Incorporation and In Vitro Release Profiles of Liquid, Deliquescent or Unstable Drugs with Fusible Excipients in Hard Gelatin Capsules", Drug Dev. Ind. Pharm., 12(10, 1553–1565 (1986).

J. R. Howard et al, "Drug Release from Thermosoftening Fatty Vehicles Filled into Hard Gelatin Capsules", Drug Dev. Ind. Pharm., 13(6) 1031–1045 (1987).

D. Bidah et al "Kinetics of *in vitro* release of sodium salicylate dispersed in Gelucire", Int. J. Pharm., 58, 215–220 (1990).

A. B. Dennis et al, "*In vivo* evaluation of rapid release and sustained release Gelucire capsule formulations", Int. J. Pharm., 65, 85–100 (1990).

C. Brossard et al, "Modelling of Theophylline Compounds Release from Hard Gelatin Capsules Containing Gelucire Matrix Granules", Drug Dev. Ind. Pharm., 17(10) 1267–1277 (1991).

V. Ratsimbazafy et al, "Les Gelucire et al ralentissement de la liberation des principes actifs", S.T.P. Pharma Prat., 1(4), 335–349 (1991).

*Primary Examiner*—Thurman K. Page
*Assistant Examiner*—Peter F. Kulkosky
*Attorney, Agent, or Firm*—Burton Rodney

[57] ABSTRACT

A sustained release captopril formulation is provided which is in the form of a capsule containing captopril in a semi-solid matrix of at least one fatty acid glyceride and/or polyethylene glycol ester. A method of preparing such a formulation is also provided.

18 Claims, No Drawings

SUSTAINED RELEASE FORMULATION CONTAINING CAPTOPRIL AND METHOD

FIELD OF THE INVENTION

The present invention relates to a sustained release formulation containing captopril as the active ingredient and to a method for preparing same.

BACKGROUND OF THE INVENTION

U.S. Pat. No. 4,105,776 to Ondetti et al discloses certain proline derivatives which includes captopril, an orally active angiotensin-converting enzyme (ACE) inhibitor, which is widely used for the treatment of hypertension, heart failure and other cardiovascular conditions. Captopril is generally available in the form of tablets which, as indicated in the Physicians' Desk Reference (PDR) 47th Edition, 1993, page 2358, is administered in a dose of from 25 to 150 mg, two or three times daily.

A once-daily captopril oral formulation would be a significant advantage over the PDR formulations for improving patient's compliance.

A variety of approaches are available for the development of prolonged release oral dosage forms. Such approaches include the use of polymers as fillers or coatings in preparing tablets, capsules, pellets, matrices (swellable or erodible) and the like. Many of these approaches have been tried in developing once daily captopril formulations with only limited success. Most recently, efforts have been directed towards investigating the colonic absorption of captopril utilizing a pulsatile drug delivery system (I. R. Wilding et al, Gastrointestinal Transit and Systemic Absorption of Captopril from a Pulsed-Release Formulation. Pharm. Res., Vol. 9, No. 5:654–657 (1992)). However, prolonged plasma levels of captopril suitable for once-a-day administration of captopril could not be obtained from these studies. Wilding et al disclose that a good percentage of captopril is probably absorbed from the upper GI tract (stomach and proximal small intestine) which explains the initial burst in the blood concentrations (high $C_{max}$ at a short $T_{max}$). The drop in captopril blood concentrations that follows may be attributable to the changes in pH in the distal portions of the GI tract. Other factors such as metabolism, interaction with ingested food, and dilution of the drug at the absorption site may also play a role. (M. Hue et al, Passive and Carrier-mediated Intestinal Absorption Components of Captopril. J. Pharm. Sci. 77:1007–1011 (1988), S. M. Singhvi et al, Effect of Food on Bioavailability of Captopril in Healthy Subjects. J. Clin. Pharmacol. 22:135–140 (1982)).

Recently, a new prototype dosage form was developed by Seta et al, whereby an oily semisolid dosage form was used to deliver captopril to humans. This system was, however, capable of delivering captopril as a twice-a-day only. This dosage form also contained ascorbic acid as an antioxidant to improve the stability of captopril. (Y. Seta et al, Design and Preparation of Captopril Sustained-release Dosage Forms and their Biopharmaceutical Properties. Int. J. Pharm. 41:245–254 (1988); Y. Seta et al, Preparation and Pharmacological Evaluation of Captopril Sustained-Release Dosage Forms Using Oily Semisolid Matrix. Int. J. Pharm. 41:255–262 (1988); Y. Seta et al, Design of Captopril Sustained-Release Preparation with Oily Semisolid Matrix Intended for Use in Human Subjects. Int. J. Pharm. 41:263–269 (1988)).

U.S. Pat. No. 5,028,432 to Chopra and Makadia (Jul. 2, 1993) discloses a pharmaceutical composition in the form of a gelatin capsule which contains ranitidine as the active-ingredient and a non-aqueous matrix containing at least one fatty acid glyceride and/or mineral oil or paraffin and preferably at least one surfactant. The fatty acid glyceride will preferably be formed of a mixture of two oil excipients, one of which is a mixture of glycerides of medium chain ($C_8$–$C_{10}$) fatty acids (such as Miglyol 812, Dynamit Nobel Co.), and the other of which is a mixture of glycerides of long chain ($C_{12}$–$C_{18}$) fatty acids such as Gelucire® materials (Gattefosse Corporation).

Sheen et al, Bioavailability of a Poorly Water-Soluble Drug From Tablet and Solid Dispersions in Humans, J. Pharm. Sci., Vol. 80, No. 7, July 1991, pp 712 to 714, disclose the use of Gelucire 44/14-polyethylene glycol (PEG) 400 mixture as a carrier for REV 5901 (α-pentyl-3-(2-quinolinylmethoxy)benzenemethanol, a 5-lipoxygenase inhibitor) in a tablet. REV 5901 is a water-insoluble drug and the Gelucire 44/14-PEG 400 mixture provided improved dissolution thereof to effect faster release.

It is also known that Gelucire® materials have been employed in the following marketed products:

Solufen 200 by SMB Galephar (worldwide)
Zenium 4.5 by SMB Galephar (Europe)
Memoxy 4.5 by SMB Galephar (Europe)
Isorday 40 by Tillotts (Switzerland)

DESCRIPTION OF THE INVENTION

In accordance with the present invention, it has been found that problems associated with prior art attempts to develop a once-a-day oral captopril formulation can be overcome by dispersing captopril in a non-aqueous semisolid matrix formed of at least one fatty acid glyceride and/or polyethylene glycol ester of a fatty acid. It has been found that the presence of the fatty acid glyceride or polyethylene glycol ester provides for sustained release of captopril, increased absorbability of captopril in the lower G.I. tract while maintaining high bioavailability of captopril, so that the captopril formulation of the invention may be administered once-a-day.

Further, in accordance with the present invention, a method is provided for preparing a once-a-day captopril formulation wherein captopril is mixed with the non-aqueous semisolid matrix material and the mixture is incorporated into a solid dosage form.

The amount of captopril present in the once-a-day formulations of the invention will be within the range of from about 10 to about 400 mg, more preferably from about 25 to about 250 mg, per unit dosage form, which preferably will take the form of a capsule or as beadlets in a capsule.

The captopril content of the captopril-non-aqueous semisolid matrix will be within the range of from about 2 to about 50% and preferably from about 5 to about 25% by weight of the filling of the capsule or beadlet. Thus, the captopril will be present in a weight ratio to the fatty acid glyceride of within the range of from about 0.02:1 to about 1:1, preferably from about 0.05:1 to about 0.3:1.

The non-aqueous semisolid matrix component is formed of glycerides of fatty acids and polyethylene glycol esters of fatty acids. Fatty acid glycerides suitable for use herein include one or more medium chain ($C_8$ to $C_{10}$) fatty acid glycerides such as one or more triglycerides of $C_8$ to $C_{10}$ fatty acids (for example, fractionated $C_8$ to $C_{10}$ coconut fatty acids). An example of a medium chain fatty acid triglyceride is Miglyol ™ 812 (Dynamit Nobel Co.).

A preferred fatty acid glyceride suitable for use herein is one or more long chain ($C_{12}$ to $C_{18}$) fatty acid glycerides (including monoesters, diesters and/or triesters of glycerol, and monoesters and/or diesters of polyethylene glycols with a mean molecular mass between about 200 and about 8000). Most preferred glycerides of long chain fatty acids and polyethylene glycol esters of long chain fatty acids for use herein are available under the name Gelucire ® (Gattefosse Corporation).

The captopril formulation of the invention may optionally include the following ingredients: a stabilizer for captopril, such as ascorbic acid, citric acid or ethylene diamine tetraacetic acid (EDTA) which may optionally be present in an amount within the range of from about 0.05 to about 10% and preferably from about 0.1 to 5% by weight of the formulation; an antioxidant for the fatty acid glyceride such as ascorbic acid, propyl gallate or butylated hydroxy toluene (BHT), which may optionally be present in an amount within the range of from about 0.005 to about 2%, and preferably from about 0.01 to about 1% by weight of the formulation;

a bioadhesive- binder such as Carbopol ® resins (B. F. Goodrich), sodium carboxymethyl cellulose, sodium alginate or polycarbophil, which may optionally be present in an amount within the range of from about 1 to about 25%, and preferably from about 2 to about 10% by weight of the formulation;

a solid polyethylene glycol having a molecular weight within the range of from about 1500 to about 8000, which may optionally be present in an amount within the range of from about 5 to about 50%, and preferably from about 10 to about 25% by weight;

a surfactant such as a sorbitan derivative (for example polysorbate 80), lecithin, Pluronic ® polyol (BASF Wyandote Corp.) or glyceryl monostearate which may optionally be present in an amount within the range of from about 1 to about 25%, and preferably from about 1 to about 10% by weight of the formulation; and optionally sweeteners and/or flavors in amounts conventionally employed.

Gelucires ®, which are the preferred non-aqueous semisolid matrix materials, are inert semisolid waxy materials which are amphiphilic in character and are available with varying physical characteristics. They are surface active in nature and disperse in aqueous media forming micelles, microscopic globules or vesicles. They are identified by their melting point/HLB value, where the HLB (Hydrophile-Lipophile Balance) value is a measure of their hydrophobic or hydrophilic nature. The lower the HLB value, the more hydrophobic is the material. The higher the HLB value, the more water-soluble it is and the faster the captopril will be released. Thus, one or a mixture of different grades of Gelucire ® materials may be chosen to achieve the desired characteristics, for example, melting point or HLB value.

Gelucires ® are polyglycolized glycerides that are prepared by the alcoholysis reaction of natural oils with polyoxyethylene glycols (PEG). They are mixtures of monoesters, diesters and/or triesters of glycerides of long chain ($C_{12}$ to $C_{18}$) fatty acids, and PEG (mono- and/or di-) esters of long chain ($C_{12}$ to $C_{18}$) fatty acids with controlled hydrophilic properties (HLB values) as well as melting points. The large family of Gelucires ® is characterized by a wide range of melting points of from about 33° to about 64° C. and preferably from about 35° to about 55° C., and by a variety of hydrophilic/lipophilic balance values, HLB, of from about 1 to about 14, preferably from about 7 to about: 14.

Specifically, the first number in the nomenclature of a Gelucire ® denotes its melting point while the second number characterizes its HLB value. For example, Gelucire ® 44/14 designates a melting point of approximately 44° C., and an HLB value of 14 to this grade of Gelucire ®. The appropriate choice of melting point/HLB value of a Gelucire ® or a mixture of Gelucires ® will provide the delivery characteristic designed for a specific function, e.g., immediate release, sustained release, and the like. The low melting points of many of the solid Gelucires ® provide a means of incorporating the captopril in them at temperatures approximately 10° C. above their respective melting points, and then filling the melt (solution and/or dispersion) in hard gelatin capsules. The melt solidifies inside capsules upon cooling to room temperature.

In the present invention, all grades of Gelucires ® may be employed. Preferred Gelucires ® for use herein are Gelucire ® 50/13, Gelucire ® 53/10 and a combination of Gelucire ® 53/10 and Gelucire ® 50/13.

Other Gelucires ® suitable for use herein include Gelucire ® 37/02, 37/06, 42/12, 44/14, 46/07, 48/09, 50/02, 50/13, and 53/10 alone or in various combinations.

In a particularly preferred formulation, from about 25 to about 250 mg captopril (per dosage form such as a capsule), will be employed in a weight ratio to Gelucire 53/10 within a range of from about 0.05:1 to about 0.3:1.

It will be appreciated that use of the Gelucire ® material as the inert carrier matrices will provide flexibility in choosing the right grade or combination of different grades so as to achieve the desired melting point and/or HLB value to provide desired once-a-day release properties to the captopril formulation of the invention.

Captopril is an acidic drug with a reactive sulfhydril group. Its absorption is also known to be amenable to variations in the pH (P. J. Worland, et al, Gastric and intestinal absorption of captopril in acutely and chronically treated rats: comparison with salicylic acid. J. Pharm. Sci., 73:1755–1758 (1984)). It is theorized that the acidic nature of this drug would allow passive absorption from the acidic environment in gastric and proximal intestinal absorption sites (where the drug is unionized) prior to its ionization (at high pH) upon its entry into the distal intestinal absorption sites. The drug is also affected by the presence of food (S. M. Singhvi, supra). These factors may affect its degradation (oxidation, formation of mixed disulfides) and thus the extent of its absorption.

It is theorized that the desired dosage form should enhance the chemical stability of captopril in the GI tract, and it should also help to minimize the detrimental interaction of the drug with food in the intestinal milieu. Thus, the utilization of a semisolid matrix as an oral drug delivery system for captopril once-a-day stems from the need to protect or stabilize the drug during its transit in the G.I. tract. Such a system has an added advantage of providing large concentrations of intact drug at a close proximity to the sites of absorption. It is believed that the semisolid matrix due to its larger size and higher density than food particles will reside closer to the gastrointestinal wall during its transit through the G.I. tract. As a consequence, it will deliver large concentrations of the drug at a close proximity to the site(s) of absorption especially the intestinal wall, thus minimizing its degradation.

The rate of release of captopril at different sites in the G.I. tract is dependent on the rate of erosion/sloughing of the Gelucire ® matrix. This characteristic is easily controlled by choosing the appropriate grade of Gelucire ® that controls its performance, namely the melting point and HLB value. As will be seen hereinafter, individual Gelucires ® and mixtures of two or more Gelucires ® can easily achieve this criteria.

It is believed that Gelucire ® matrices will protect the drug (captopril) against the effect of food and pH changes throughout its transit path in the G.I. tract, and upon erosion of the matrix in different parts of the G.I. tract, captopril will be protected inside micelles or microscopic globules or vesicles. Chemical stabilizers may further improve this effect when incorporated in the formulation.

A slow sloughing of the hydrated surface of the Gelucire ® matrix occurs near the surface of the G.I. membrane which would result in a high concentration gradient of the drug at close proximity to the site of absorption. This could prove to be a factor in improving the absorption of captopril by passive diffusion.

The location of release of captopril depends on the rate of transit of the semisolid matrix. The rate of erosion/sloughing of the matrix should also be such that all the captopril is released during the transit of the semisolid matrix from stomach to the colon.

It is believed that adherence of the formulation to the surface of the membranes due to the bioadhesive nature or stickiness of Gelucire ® and/or due to the presence of additional bioadhesive materials will prolong the transit time and will thereby increase the formulation's retention time in the stomach or upper G.I. tract. This property, inherent or enhanced, would prove beneficial for delivering captopril as a once-a-day formulation. The rate of erosion/sloughing of the matrix so as to ensure the complete release of captopril during its transit in the G.I. tract may be controlled, as mentioned above, by the choice of Gelucires ®.

In a preferred embodiment, the captopril formulation of the invention is formed of a gelatin capsule filled with captopril solubilized or uniformly dispersed in a non-aqueous-semisolid matrix containing at least one fatty acid glyceride and/or polythylene glycol ester which is a Gelucire ® material as described herein, preferably Gelucire ® 50/13, Gelucire ® 53/10 or a combination of Gelucire ® 50/13 and Gelucire ® 53/10, in a weight ratio of 50/13:53/10 of within the range of from about 9:1 to about 0.1:1, preferably from about 3:1 to about 0.3:1. The captopril will be present in a weight ratio to the Gelucire ® non-aqueous semisolid matrix of within the range of from about 0.02:1 to about 1:1, preferably from about 0.05:1 to about 0.3:1.

In forming the sustained released captopril formulation of the invention, the captopril is dissolved or dispersed uniformly in a melt of the fatty acid glyceride(s). The mixture in the form of a melt containing this desired semisolid matrix and captopril dispersed therein may be filled into hard or soft gelatin capsules. Alternatively, the semisolid matrix, including the captopril, may be powdered by milling at a low temperature and then incorporated into tablets, beads or beadlets employing conventional procedures. The beads or beadlets may also be formed by the process of prilling where the melt is added dropwise to a non-miscible liquid maintained at a lower temperature.

The captopril compositions of the invention are intended for human use and may be administered once-a-day in a dosage to control hypertension.

The following Examples represent preferred embodiments of the invention. Unless otherwise indicated, all temperatures are expressed in degrees Centigrade (° C.).

EXAMPLES 1 TO 10

A. Preparation of Captopril-Gelucire ® Formulations

Different captopril/Gelucire ® formulations were prepared by melting the Gelucire(s) ® in a 250 mL Erlenmeyer flask. The weight of the melt was estimated from the number of capsules intended to be filled. Usually 50 to 70 capsules were prepared at a Gelucire(s) ® weight of 560 mg/capsule. The waxy mixture was heated at 10° C.–15° C. above the calculated melting point, while a small magnetic stirrer ensured proper mixing. Captopril was added slowly to the melt with continuous mixing until all captopril dissolved. The melt was then filled in size #0 white opaque hard gelatin capsules at a total captopril-Gelucire ® weight of 610 mg/capsule. The melt was left to solidify or congeal at room temperature.

The Example 9 formulation, a preferred formulation, was prepared by melting Gelucire 53/10 at about 60° to 70° C. and then dissolving and/or dispersing captopril in the melt. The liquid solution/suspension was then filled into hard gelatin capsules, and the contents of the capsules hardened or solidified upon cooling to room temperature.

The various compositions prepared are shown in Table I set out below.

TABLE I

Composition of Formulations of Captopril/Gelucires ® (Total capsule weight is 610 mg)
Example No. and Composition of Formulations expressed in milligrains/capsule

| Component | 1 | 2 | 3 | 4 | 5 | 6 | 9 | 8 | 9 | 10 |
|---|---|---|---|---|---|---|---|---|---|---|
| Captopril | 50 | 50 | 50 | 50 | 50 | 50 | 50 | 50 | 50 | 50 |
| Gelucire 44/14 | 112 (20%)* | — | — | 112 (20%) | — | 280 (50%) | — | — | — | — |
| Gelucire 50/13 | 448 (80%) | 560 (100%) | — | — | 280 (50%) | — | 420 (75%) | 280 (50%) | — | 140 (25%) |
| Gelucire 48/09 | — | — | 560 (100%) | 448 (80%) | 280 (50%) | 280 (50%) | — | — | — | — |
| Gelucire 53/10 | — | — | — | — | — | — | 140 (25%) | 280 (50%) | 560 (100%) | 420 (75%) |
| Total Weight (mg) | 610 | 610 | 610 | 610 | 610 | 610 | 610 | 610 | 610 | 610 |
| Calculated** | 48.8/13.2 | 50/13 | 48/09 | 47.2/10.0 | 49/11.5 | 46/11.5 | 50.75/12.25 | 51.5/11.5 | 53/10 | 52.25/10.75 |

TABLE I-continued

Composition of Formulations of Captopril/Gelucires ® (Total capsule weight is 610 mg)

Example No. and Composition of Formulations expressed in milligrams/capsule

| Component | 1 | 2 | 3 | 4 | 5 | 6 | 9 | 8 | 9 | 10 |
|---|---|---|---|---|---|---|---|---|---|---|
| m.p./HLB | | | | | | | | | | |

*Values in brackets denote the relative percent composition of Gelucires ®.
**An estimate of the melting point (m.p.) and the HLB value of each combination of Gelucire ® matrix was calculated as follows:
Calculated m.p. = m.p. of Component 1 × % composition of Component 1 + m.p. of Component 2 × % composition of Component 2, and the like.
Calculated HLB = HLB of Component 1 × % composition of Component 1 + HLB of Component 2 × % composition of Component 2, and the like.

B. In Vitro Dissolution Procedure

1. Dissolution screening methods

Two dissolution methods, namely, the USP Basket Method (Apparatus I) at 50 and 100 RPM and the USP Paddle Method (Apparatus II) at 50 RPM, were used to screen the different formulations. Simulated gastric fluid (SGF, 0.1N HCl, pH=1.2, no enzyme added) was used primarily as the dissolution medium due to the good stability of captopril at low pH. Water and simulated intestinal fluid (SIF, pH=7.4 buffer, no enzyme added) were also used and the solutions (1000 mL in each vessel) were kept heated at 37° C. Ten samples of 1.0 mL each were automatically collected at different sampling points. Sampling times varied according to the formulation tested, and generally ranged from 0 to 20 hours with intervals of 30 minutes, 1 hour, or 2 hours.

2. Dissolution Methodology

One liter of the dissolution medium was added to each of six dissolution vessels, and was left to equilibrate at 37° C. ±0.5° C. Either 3 or 6 capsules were tested for each formulation by placing one capsule in each vessel. The test was started by lowering the paddles or baskets into the media to a preset height and activating a programmed autosampler at the same time. The samples were automatically analyzed to quantitate captopril dissolved by a specific HPLC method.

RESULTS AND DISCUSSION

Table I summarizes the compositions of the different formulations thus prepared. Each prototype formulation contained 50 mg captopril in 560 mg of the Gelucire(s) ®. After preparation, the formulations were left at least one day at room temperature before any dissolution run was carried out. The dissolution profiles are presented as average of the percent drug label dissolved at the different sampling times. Two dissolution criteria identified to assess each formulation, namely, $T_{90}$ and $T_{50}$ (time for 90% and 50% of label to dissolve) are shown in Table II. If the time for the 90% dissolution of the drug was 12 hours or more, this was considered a once-a-day formulation. The reason for this is that significant plasma levels of captopril will be maintained at least for the same period of time, thus exhibiting a direct therapeutic response, and after this period, the therapeutic response will be induced for at least another eight hours by the pharmacodynamic effect of the drug (C. Richer et al, Captopril: Pharmaco-kinetics, Antihypertensive and Biological Effects in Hypertensive Patients. British Journal of Clinical Pharmacology, 17, 243–250 (1984)). It has been reported that the pharmacological effects of captopril last even when it disappears from the plasma because the angiotensin converting enzyme (ACE) requires 6–8 hours to return to its normal levels after depletion and/or due to slow in vivo reconversion of captopril in tissues from the metabolite captopril disulfides (C. Richer et al, supra.).

Discussion of the different variables, e.g. matrix composition, dissolution medium, dissolution method, agitation rates and their effect on the dissolution behavior of the different prototypes are summarized below.

1. Composition

Table I summarizes the composition of Examples 1 to 10 formulations with long captopril release time that were prepared. The dissolution characteristics of these formulations are summarized in Table II.

TABLE II

Summary of the Dissolution Parameters, $T_{50}$* and $T_{90}$*, of Different Captopril/Gelucires ® Prolonged Release Formulations in Simulated Gastric Fluid (0.1 N HCl, pH = 1.2)

| Formulation with Storage Time and Temperature | Dissolution Times | | | | | |
|---|---|---|---|---|---|---|
| | Basket 100 RPM | | Basket 50 RPM | | Basket 50 RPM | |
| | $T_{50}$ | $T_{90}$ | $T_{50}$ | $T_{90}$ | $T_{50}$ | $T_{90}$ |
| Example 1 | | | | | | |
| 1 Day, RT** | — | — | 226 min | 690 min. | — | — |
| 12 Days, RT | — | — | 190 min. | 600 min. | — | — |
| Example 2 | | | | | | |
| 4 Days, RT | 275 min. | 680 min. | — | — | — | — |
| 13 Days, RT | — | — | — | — | 180 min | 580 min. |
| 25 Days, RT | — | — | 250 min. | 680 min. | — | — |
| Example 3 | | | | | | |
| 3 Days, RT | 675 min. | — | — | — | — | — |
| Example 4 | | | | | | |
| 2 Days, RT | 360 min. | 1170 min. | — | — | — | — |
| 6 Days, RT | — | — | — | — | 330 min. | 960 min. |
| Example 5 | | | | | | |
| 1 Days, RT | 325 min. | 1040 min. | — | — | — | — |
| 5 Days, RT | — | — | — | — | 280 min. | 800 min. |
| Example 6 | | | | | | |
| 1 Day, RT | — | — | — | — | 200 min. | 85% at 720 min. |
| Example 7 | | | | | | |
| 4 days, RT | — | — | 280 min. | 680 min. | 200 min. | 570 min. |

TABLE II-continued

Summary of the Dissolution Parameters, $T_{50}$* and $T_{90}$*, of Different Captopril/
Gelucires ® Prolonged Release Formulations in Simulated Gastric Fluid
(0.1 N HCl, pH = 1.2)

| Formulation with Storage Time and Temperature | Dissolution Times | | | | | |
|---|---|---|---|---|---|---|
| | Basket 100 RPM | | Basket 50 RPM | | Basket 50 RPM | |
| | $T_{50}$ | $T_{90}$ | $T_{50}$ | $T_{90}$ | $T_{50}$ | $T_{90}$ |
| Example 8 | | | | | | |
| 1 Day, RT | — | — | 270 min. | 670 min. | 260 min. | 750 min. |
| 5 Days, RT | — | — | 250 min. | 720 min. | — | — |
| Example 9 | | | | | | |
| 2 Days, RT | — | — | 420 min. | 1180 min. | 480 min. | 80% at 1200 min. |
| 10 Days, RT | 440 min. | 1200 min. | — | — | — | — |
| Example 10 | | | | | | |
| 3 Days, RT | — | — | 410 min. | 900 min. | 350 min. | 1200 min. |
| 6 Days, RT | 390 min. | 960 min. | — | — | — | — |

*Time needed for 50% and 90% of label drug released.
**Room temperature (23 ± 2° C.)

The Example 1 formulation containing 20% Gelucire ® 44/14 and 80% Gelucire ® 50/13 showed prolonged release with 90% of the label ($T_{90}$) being released at 10 to 11.5 hours.

Example 3 formulation for example with 100% Gelucire ® 48/09 showed prolonged release times with only 50% of the label ($T_{50}$) being released at 11.0 hours using the basket method at a stirring rate of 100 rpm. The shape of the matrix (plug) remained unchanged, and the surface was slightly hydrated and soft (swollen). Under the same conditions, Example 2 formulation prepared with 100% Gelucire ® 50/13, eroded completely with a $T_{90}$ of 11 hours. Since the melting points of these two Gelucires are very close, the difference in the dissolution behavior between these two formulations was clearly due to the difference in their HLB values.

A variety of formulations were prepared by mixing different ratios of Gelucire ® 50/13, 48/09, and 44/14. The dissolution behavior of these formulations was assessed using both dissolution methods. The paddle method at 50 rpm was utilized as a more rigorous agitation condition than the basket method. It was concluded that Gelucire ® 50/13 was a good component to achieve a $T_{90}$ of 11–12 hours due to its high m.p. and HLB values.

In order to prolong the release rate to a $T_{90}$ of 18–20 hours, Gelucire ® 53/10 was used to prepare a new set of formulations (Examples 7 to 10). It was clearly noticed that the gradual percent increase in the Gelucire ® 53/10 ratio prolonged the $T_{90}$ to the desired range of 18–20 hours. The in vitro dissolution behavior of some formulations was not tested due to their low melting points (below 50° C.). It was theorized that a formulation with a high melting point will not disintegrate or be crushed due to the motility of the G.I. tract. Thus, the Examples 2 and 9 formulations were chosen to prolong the dissolution $T_{90}$ to about 11 and 20 hours, respectively. These two formulations were sent for in vivo bioavailability testing in dogs.

2. Effect of Experimental Conditions (Stirring/Dissolution media)

Initially, the USP basket method at 50 rpm was used as the screening dissolution method. Although this method proved to be applicable for in vitro screening, more rigorous conditions were employed for screening the newer prototypes with longer release profiles. USP basket method at 100 rpm and USP paddle method at 50 rpm were also used to screen Examples 2 to 10 formulations. The results are summarized in Table II as $T_{50}$ and $T_{90}$ values. Table II shows clearly the effect of increasing the concentration of Gelucire ® 53/10 on prolonging the release rate of captopril. In general, the values obtained using the paddle method were smaller, i.e., faster dissolution rates than when using the baskets at both speeds. The exceptions to this trend were Examples 9 and 10 formulations where the dissolution rates were slower. This behavior is explained by the fact that at higher concentrations of Gelucire ® 53/10, the melting points are increasing with a concomitant decrease in the HLB values. The capsules were harder, maintaining their shape, and were less affected by the rate of agitation. In reality, the capsules were hydrated and swollen with less sloughing at high ratios of Gelucire ®53/10. This characteristic of the capsule, sturdy but sloughable, is desirable for in vivo application. A sturdy formulation will withstand the adverse effects of the G.I. motility better, thus, the initial crushing of a soft formulation and the untimely release of the drug will be prevented. Sloughing of thin films of the hydrated surface of the capsule, due to the G.I. motility and the presence of food, will play a major role in delivering the drug to the sites of absorption along the walls of the G.I. tract. Thus, the degree and extent of this process will determine the degree of bioavailability of captopril. Use of Gelucire ® matrix will keep the drug protected within the excipient and deliver it, when sloughed, at a close proximity to the walls of the G.I. tract.

Due to the increased stability of captopril at low pH, simulated gastric fluid (SGF, 0.1N HCl, pH 1.2) was used most frequently as dissolution medium. Simulated intestinal fluid (SIF, pH 7.4) was also used to check the effect of the different dissolution media on the release profile.

From the above, it is seen that the captopril formulation of the invention which includes at least one fatty acid glyceride and/or polyethylene glycol ester, preferably a long chain fatty acid glyceride ($C_{12}$ to $C_{18}$) and/or polyethylene glycol ester of a long chain ($C_{12}$ to $C_{18}$) fatty acid provides a once-a-day captopril delivery system.

What is claimed is:

1. A sustained release once-a-day oral captopril formulation comprising a therapeutically effective amount of captopril and a non-aqueous semisolid matrix therefor to impart sustained release properties to the captopril, wherein the non-aqueous semisolid matrix is a fatty acid glyceride and/or a polyethylene glycol ester of a fatty acid.

2. The formulation as defined in claim 1 wherein the semisolid matrix is a long chain fatty acid glyceride and/or a polyethylene glycol ester of a long chain fatty acid.

3. The formulation as defined in claim 2 wherein the semisolid matrix is one or a mixture of long chain ($C_{12}$ to $C_{18}$) fatty acid glycerides and/or polyethylene glycol esters of ($C_{12}$ to $C_{18}$) fatty acids.

4. The formulation as defined in claim 3 wherein the semisolid matrix is a mixture of mono-, di- and/or triglycerides of $C_{12}$ to $C_{18}$ fatty acids and/or monoesters and/or diesters of polyethylene glycols of $C_{12}$ to $C_{18}$ fatty acids.

5. The formulation as defined in claim 4 wherein the semisolid matrix has a melting point within the range of from about 33° to about 64° C. and a hydrophilic/lipophilic value (HLB) of within the range of from about 1 to about 14.

6. The formulation as defined in, claim 5 wherein the semisolid matrix has a melting point of from about 35 to about 55 and an HLB value of from about 7 to about 14.

7. The formulation as defined in claim 6 wherein the semisolid matrix has a melting point of from about 44° to about 53° C. and an HLB value of from about 10 to about 14.

8. The formulation as defined in claim 7 wherein the semisolid matrix has a melting point of about 50° C. and an HLB value of about 13, a melting point of about 53° C. and an HLB value of about 10 or is a combination of two semisolid matrices having a melting point of about 53° C. and an HLB value of about 10 and a melting point of about 44° C. and an HLB value of about 14.

9. The formulation as defined in claim 1 which is administered once daily.

10. The formulation as defined in claim 1 wherein the fatty acid glyceride is a medium chain fatty acid glyceride.

11. The formulation as defined in claim 1 wherein the captopril is present in a weight ratio to the semisolid matrix within the range of from about 0.02:1 to about 1:1.

12. The formulation as defined in claim 1 in the form of a capsule filled with captopril and a semisolid matrix.

13. The formulation as defined in claim 1 in the form of a tablet or as beadlets contained in a capsule.

14. A once-a-day oral captopril formulation comprising a therapeutically effective amount of captopril and a semisolid matrix which is one or a mixture of long chain fatty acid glycerides and/or one or a mixture of polyethylene glycol esters of long chain fatty acids.

15. The once-a-day captopril formulation as defined in claim 14 wherein the semisolid matrix is a $C_{12}$ to $C_{18}$ fatty acid glyceride and/or a $C_{12}$ to $C_{18}$ fatty acid ester of a polyethylene glycol.

16. The once-a-day captopril formulation as defined in claim 15 wherein the $C_{12}$ to $C_{18}$ fatty acid glyceride is a mixture of mono- di- and/or triglycerides and/or a mixture of monoesters and/or diesters of polyethylene glycol and a long chain fatty acid, said mixture having a melting point within the range of from about 33° to about 64° C. and a hydrophilic/lipophilic balance (HLB) value of within the range of from abut 1 to about 14.

17. A method for forming a once-a-day oral captopril formulation, which comprises mixing captopril and a fatty acid glyceride and/or a fatty acid ester of a polyethylene glycol and forming the mixture into a solid dosage form.

18. The method as defined in claim 17 wherein the fatty acid glyceride is a mixture of mono-, di- and/or triglycerides and/or monoesters and/or diesters of polyethylene glycol and a long chain fatty acid, said mixture having a melting point within the range of from about 33° to about 64° C. and a hydrophilic/lipophilic balance (HLB) value of within the range of from about 1 to about 14.

* * * * *